United States Patent
Merrill et al.

(10) Patent No.: US 8,021,704 B2
(45) Date of Patent: Sep. 20, 2011

(54) FOOD INGREDIENTS AND FOOD PRODUCTS TREATED WITH AN OXIDOREDUCTASE AND METHODS FOR PREPARING SUCH FOOD INGREDIENTS AND FOOD PRODUCTS

(75) Inventors: Richard K. Merrill, Highlands Ranch, CO (US); Mayank Singh, Aurora, CO (US)

(73) Assignee: Leprino Foods Company, Denver, CO (US)

( * ) Notice: Subject to any disclaimer, the term of this patent is extended or adjusted under 35 U.S.C. 154(b) by 112 days.

(21) Appl. No.: 12/471,054

(22) Filed: May 22, 2009

(65) Prior Publication Data

US 2009/0238917 A1    Sep. 24, 2009

Related U.S. Application Data

(62) Division of application No. 11/176,634, filed on Jul. 6, 2005, now abandoned.

(60) Provisional application No. 60/586,193, filed on Jul. 7, 2004.

(51) Int. Cl.
    A23C 9/12    (2006.01)
    A23C 19/00   (2006.01)

(52) U.S. Cl. ............... 426/36; 426/34; 426/42; 426/582

(58) Field of Classification Search .................... 426/34, 426/36, 38, 40, 42, 580, 582
    See application file for complete search history.

(56) References Cited

U.S. PATENT DOCUMENTS

| | | | |
|---|---|---|---|
| 1,748,781 A | 2/1930 | Martin | |
| 2,688,553 A | 9/1954 | Schicks et al. | |
| 3,741,774 A | 6/1973 | Burkwall, Jr. | |
| 3,862,005 A * | 1/1975 | Miyake et al. | 435/137 |
| 3,961,077 A | 6/1976 | Kielsmeier | |
| 3,998,700 A | 12/1976 | Reinbold et al. | |
| 4,085,228 A | 4/1978 | Reinbold et al. | |
| 4,137,397 A | 1/1979 | Dutta et al. | |
| 4,244,983 A | 1/1981 | Baker | |
| 4,268,528 A | 5/1981 | Montigny | |
| 4,339,468 A | 7/1982 | Kielsmeier | |
| 4,343,817 A | 8/1982 | Swanson et al. | |
| 4,372,979 A | 2/1983 | Reinbold et al. | |
| 4,459,313 A | 7/1984 | Swanson et al. | |
| 4,460,609 A | 7/1984 | Kristiansen et al. | |
| 4,552,774 A | 11/1985 | Gronfor | |
| 4,592,274 A | 6/1986 | Tomatis | |
| 4,608,921 A | 9/1986 | Mongiello, Sr. | |
| 4,626,439 A | 12/1986 | Meyer | |
| 4,665,811 A | 5/1987 | Meyer | |
| 4,753,815 A | 6/1988 | Kielsmeier et al. | |
| 4,894,245 A | 1/1990 | Kielsmeier et al. | |
| 4,898,745 A | 2/1990 | Zamzow et al. | |
| 4,919,943 A | 4/1990 | Yee et al. | |
| 4,937,091 A | 6/1990 | Zallie et al. | |
| 4,957,749 A | 9/1990 | Prieels et al. | |
| 4,959,229 A | 9/1990 | Reddy et al. | |
| RE33,508 E | 12/1990 | Kielsmeier et al. | |
| 4,997,670 A | 3/1991 | Kielsmeier et al. | |
| 5,030,470 A | 7/1991 | Kielsmeier et al. | |
| 5,080,913 A | 1/1992 | Gamay | |
| 5,094,873 A | 3/1992 | Kerrigan et al. | |
| 5,104,675 A | 4/1992 | Callahan et al. | |
| 5,108,773 A | 4/1992 | Smith et al. | |
| 5,200,216 A | 4/1993 | Barz et al. | |
| 5,215,778 A | 6/1993 | Davison et al. | |
| 5,225,200 A | 7/1993 | Gamay | |
| 5,234,700 A | 8/1993 | Barz et al. | |
| 5,234,707 A | 8/1993 | Merkenich et al. | |
| 5,240,724 A | 8/1993 | Otto et al. | |
| 5,244,687 A | 9/1993 | Rybinski et al. | |
| 5,266,340 A | 11/1993 | Samson et al. | |
| 5,277,926 A | 1/1994 | Batz et al. | |
| 5,330,780 A | 7/1994 | Yee et al. | |
| 5,336,765 A | 8/1994 | Au et al. | |
| 5,350,595 A | 9/1994 | Hockenberry et al. | |
| 5,374,443 A | 12/1994 | Jackson et al. | |
| 5,380,543 A | 1/1995 | Barz et al. | |
| 5,395,630 A | 3/1995 | Gamay | |

(Continued)

FOREIGN PATENT DOCUMENTS

WO    WO 2002-089592 A1    11/2002

(Continued)

OTHER PUBLICATIONS

Breene et al., Manufacture of pizza cheese without starter, 1964, Journal of Dairy Science, 47:1173-1180.*

(Continued)

*Primary Examiner* — Leslie Wong
(74) *Attorney, Agent, or Firm* — Kilpatrick Townsend & Stockton LLP

(57) ABSTRACT

A method of making an aldobionate product is described. The method may include providing a milk product having one or more reducing sugars, and maintaining a pH of the milk product at about 5.5 or more by adding a buffer compound to the milk product. The method may also include adding an oxidoreductase enzyme to the milk product, where at least a portion of the reducing sugar is oxidized into the aldobionate product. In addition, a method of making an aldobionate product is described that includes the steps of providing a milk product comprising a reducing sugar, mixing oxygen into the milk product, and adding an oxidoreductase enzyme to the milk product, where at least a portion of the reducing sugar is oxidized into the aldobionate product.

28 Claims, 5 Drawing Sheets

U.S. PATENT DOCUMENTS

| | | | |
|---|---|---|---|
| 5,401,518 | A | 3/1995 | Adams et al. |
| 5,413,804 | A | 5/1995 | Rhodes |
| 5,431,931 | A | 7/1995 | Nauth et al. |
| 5,431,946 | A | 7/1995 | Vesely et al. |
| 5,462,755 | A | 10/1995 | Mehnert |
| 5,466,477 | A | 11/1995 | Sevenich |
| 5,470,595 | A | 11/1995 | Kopp et al. |
| 5,480,666 | A | 1/1996 | Lindgren |
| 5,484,618 | A | 1/1996 | Barz et al. |
| 5,520,934 | A | 5/1996 | Meilleur |
| 5,527,549 | A | 6/1996 | Bernacchi et al. |
| 5,529,795 | A | 6/1996 | Aldrovandi |
| 5,532,018 | A | 7/1996 | Miller et al. |
| 5,549,916 | A | 8/1996 | Gamay |
| 5,567,464 | A | 10/1996 | Barz et al. |
| 5,601,760 | A | 2/1997 | Rosenberg |
| 5,709,900 | A | 1/1998 | Miller et al. |
| 5,750,177 | A | 5/1998 | Yee et al. |
| 5,766,657 | A | 6/1998 | Farkye et al. |
| 5,895,671 | A | 4/1999 | Adamany et al. |
| 5,902,625 | A | 5/1999 | Barz et al. |
| 5,906,854 | A | 5/1999 | Scherping et al. |
| 5,925,398 | A | 7/1999 | Rizvi et al. |
| 5,942,263 | A | 8/1999 | Chen et al. |
| 5,952,030 | A | 9/1999 | Nelles et al. |
| 5,967,026 | A | 10/1999 | Nelles et al. |
| 6,079,323 | A | 6/2000 | Dzenis |
| 6,086,926 | A | 7/2000 | Bruce et al. |
| 6,120,809 | A | 9/2000 | Rhodes |
| 6,143,334 | A | 11/2000 | Reinbold et al. |
| RE37,264 | E | 7/2001 | Chen et al. |
| 6,303,160 | B1 | 10/2001 | Laye et al. |
| 6,319,526 | B1 | 11/2001 | Dahlstrom et al. |
| 6,322,841 | B1 | 11/2001 | Jackson et al. |
| 6,326,038 | B1 | 12/2001 | Bradford et al. |
| 6,358,543 | B1 | 3/2002 | Soe et al. |
| 6,358,551 | B1 | 3/2002 | Sadowsky, IV et al. |
| 6,372,268 | B1 | 4/2002 | Silver et al. |
| 6,426,102 | B1 | 7/2002 | Isom et al. |
| 6,440,481 | B1 | 8/2002 | Gascoigne et al. |
| 6,455,081 | B1 | 9/2002 | Han et al. |
| 6,475,538 | B2 | 11/2002 | Thakar et al. |
| 6,475,638 | B1 | 11/2002 | Mitsuhashi et al. |
| 6,506,426 | B2 | 1/2003 | Adamany et al. |
| 6,536,691 | B2 | 3/2003 | Prewitt et al. |
| 6,645,542 | B2 | 11/2003 | Nelles et al. |
| 6,773,740 | B2 | 8/2004 | Hyde et al. |
| 6,872,412 | B2 | 3/2005 | Soe et al. |
| 6,998,145 | B2 | 2/2006 | Henry et al. |
| 2003/0104106 | A1 | 6/2003 | Trecker et al. |
| 2004/0018292 | A1 | 1/2004 | Lindstrom et al. |
| 2004/0076729 | A1 | 4/2004 | Jaskulka |
| 2005/0249853 | A1 | 11/2005 | Merrill et al. |
| 2005/0249854 | A1 | 11/2005 | Merrill et al. |
| 2005/0271789 | A1 | 12/2005 | Merrill et al. |
| 2006/0008555 | A1 | 1/2006 | Merrill et al. |
| 2006/0204643 | A1 | 9/2006 | Merrill et al. |

FOREIGN PATENT DOCUMENTS

| | | | |
|---|---|---|---|
| WO | WO 2005-104859 | A2 | 11/2005 |

OTHER PUBLICATIONS

Miyamoto et al., Production of Lactobionic acid from whey by *Pseudomonas* sp., LS13-1, Biotechnology Letters 22, XP-002350037, Kluwer Academic Publishers 2000, pp. 427-430.

Murakami et al., "Fermentative Production of Lactobionic Acid by *Burkholderia cepacia*", J. Appl. Glycosci #50, XP008036393, The Japanese Society of Applied Glycoscience 2003, pp. 117-120.

Rand, Jr., et al., "Direct Enzymatic Conversaion of Lactose in Milk to Acid," XP 000644502, Journal of Dairy Science, vol. 58, No. 8, pp. 1144-1150.

Scott, R., "Chapter 13—Cheesemaking Operations," Cheesemaking Practice, Second Edition, pp. 2 cover pages and 186-212, 1986.

* cited by examiner

FOOD INGREDIENTS AND FOOD PRODUCTS TREATED WITH AN OXIDOREDUCTASE AND METHODS FOR PREPARING SUCH FOOD INGREDIENTS AND FOOD PRODUCTS

CROSS-REFERENCES TO RELATED APPLICATIONS

This application is a divisional of U.S. patent application Ser. No. 11/176,634, filed Jul. 6, 2005 now abandoned and entitled "Food Ingredients and Food Products Treated with an Oxidoreductase and Methods for Preparing Such Food Ingredients and Food Products," which claims priority to U.S. Provisional Patent Application Ser. No. 60/586,193, filed Jul. 7, 2004 and entitled "Food Ingredients and Food Products Treated with an Oxidoreductase and Methods for Preparing Such Food Ingredients and Food Products," the entire contents of both applications are herein incorporated by reference for all purposes.

This application is also related to the following U.S. Patent Applications, all of which are incorporated herein by reference in their entirety for all purposes:
1. U.S. Provisional Patent App. No. 60/568,029, filed May 3, 2004, entitled "SOFT OR FIRM/SEMI-HARD RIPENED OR UNRIPENED CHEESE AND METHODS OF MAKING SUCH CHEESES".
2. U.S. Provisional Patent App. No. 60/568,022, filed May 3, 2004, entitled "SOFT OR FIRM/SEMI-HARD RIPENED OR UNRIPENED BLENDED CHEESES AND METHODS OF MAKING SUCH CHEESES".
3. U.S. Provisional Patent App. No. 60/568,017, filed May 3, 2004, entitled "METHODS OF MAKING SOFT OR FIRM/SEMI-HARD RIPENED OR UNRIPENED CHEESES".
4. U.S. patent application Ser. No. 11/121,537, filed May 3, 2005, now U.S. Pat. No. 7,585,537, entitled "Cheese and Methods of Making Such Cheese,".
5. U.S. patent application Ser. No. 11/122,283, filed May 3, 2005, now U.S. Pat. No. 7,651,715, entitled "Blended Cheeses and Method for Making Such Cheeses,"
6. U.S. patent application Ser. No. 11/121,398, filed May 3, 2005, now U.S. Pat. No. 7,579,033, entitled "Methods for Making Soft or Firm/Semi-Hard Ripened and Unripened Cheese and Cheeses Prepared by Such Methods,".
7. U.S. patent application Ser. No. 10/977,540, filed Oct. 29, 2004, now U.S. Pat. No. 7,494,677, entitled "Coated Food Products and Methods of Producing Coated Food Products with Reduced Permeability to Fat and Oil,".

BACKGROUND

Reducing carbohydrates are present in a wide variety of foods, including fruits, breads, and dairy products (e.g., milk and cheese), among many other kinds of food. These reducing carbohydrates include reducing sugars, such as glucose, galactose, lactose, and other saccharides having an unsubstituted anomeric center, that add flavor and metabolizable energy to the food. However, reducing sugars in food ingredients also present challenges in the preparation of cooked (e.g., baked) foods.

The heating of reducing sugars often leads to non-oxidative, non-enzymatic browning of the food through processes such as carmelization (i.e., the direct heating of carbohydrates in the presence of acids or salts), and Maillard browning (i.e., the interaction of amino group containing compounds such as proteins with the reducing sugar and water). Maillard browning is a common problem in the cooking of breads and dairy foods where the starting ingredients invariably include reducing sugars, amino acids (e.g., L-lysine, L-arginine, L-histidine, etc.) and water, mixed together and reacting at elevated temperatures to cause the browning.

The control of Maillard browning is important for several reasons: Overly browned foods may be aesthetically undesirable and unappetizing, especially when the dark colors are accompanied by unwanted odors and flavors. Also, the reactions that produce Maillard browning reduce the quantity of essential amino acids in the food, reducing its overall nutrient value.

Undesirable Maillard browning may be controlled by changing the water content in the starting ingredients of the food, where less water generally reduces the degree of browning. For liquid ingredients, Maillard browning may be reduced by lowering the pH (i.e., increasing the acidity) of the ingredient. The browning may also be reduced by lowering the cooking temperature of the food. Finally, food additives such as sulfur dioxide or sulfites may be added prior to or during cooking to inhibit Maillard browning.

Unfortunately, all of these means of controlling Maillard browning create other problems when cooking the foods, including overly dry baked goods due to removal of water, and sour tastes in foods due to lowering the pH. Thus, there remains a need for new approaches for controlling Maillard browning that do not add unnatural chemical additives to the food, or adversely affect the taste and quality of the food.

BRIEF SUMMARY

Compositions for use in the preparation of cheese are described. The compositions may include a cheese ingredient and an oxidoreductase enzyme.

Methods of controlling browning of a cheese in a cheese-containing foodstuff during heating are also described. The methods may include the steps of (a) providing a foodstuff comprising a cheese, where the cheese comprises an oxidoreductase enzyme in an amount effective to prevent excessive browning of the cheese during heating, and (b) heating the foodstuff for a time sufficient to melt the cheese.

Cooked foodstuffs made by a process that includes the steps of forming an uncooked mixture by combining one or more food ingredients that comprise a reducing sugar with an oxidoreductase enzyme and heating the uncooked mixture to make the cooked foodstuff are also described. The oxidoreductase enzyme oxidizes at least a portion of the reducing sugar.

Methods of making an aldobionic acid are also described. The methods include the steps of obtaining a whey fraction from a mixture of curds and whey; separating the whey fraction into a whey permeate and a retentate; oxidizing reducing sugar in the whey permeate by the addition of an oxidoreductase enzyme to the whey permeate; and oxidizing the reducing sugar to form the aldobionic acid.

Methods of treating the whey protein retentate with oxidoreductase enzymes are also described. The methods include adding oxidoreductase enzymes to whey protein retentate that is separated from the liquid whey permeate. The enzymes catalyze the oxidation of reducing sugars in the retentate to lactones and hydrogen peroxide, which can act as a peroxide preservative in the whey protein. The oxidoreductase treated whey protein retentate may be used to make coatings in foodstuffs.

Methods of cooking foodstuffs that reduce the absorption of fats or oils into the foodstuffs are also described. The methods may include the steps of (a) providing a foodstuff coated with a whey composition comprising a whey protein and one or more reducing sugars treated with oxidoreductase enzymes, where the whey protein comprises one or more proteins present in, or derived from, whey; and (b) heating the coated foodstuff in the fat or oil, whereby the whey composition forms a film on the foodstuff to reduce the absorption of the fat or oil by the coated foodstuff relative to a corresponding uncoated foodstuff, and whereby the treated reducing sugars result in less browning during the heating step.

Anti-caking compositions that include an anti-caking agent; and an oxidoreductase enzyme are also described.

Foodstuff compositions are also described that include an oxidoreductase enzyme and a catalase enzyme, where the enzymes create a sugar oxidization cycle where the oxidoreductase enzyme oxidizes a reducing sugar to a lactone, and a hydrogen peroxide that is converted by the catalase into oxygen ($O_2$) and water, where the oxygen generated by the catalase is used to further the reaction catalyzed by the oxidoreductase to remove the reducing sugar from the foodstuff composition.

Embodiments also include methods of making an aldobionate product, where the method include the steps of providing a milk product comprising a reducing sugar, and maintaining a pH of the milk product at about 5.5 or more by adding a buffer compound to the milk product. The method may also include adding an oxidoreductase enzyme to the milk product, where at least a portion of the reducing sugar is oxidized into the aldobionate product.

Embodiments of the invention further include methods of making an aldobionate product that include the steps of providing a milk product comprising a reducing sugar, and mixing oxygen into the milk product. The method may also include adding an oxidoreductase enzyme to the milk product, where at least a portion of the reducing sugar is oxidized into the aldobionate product.

Embodiments of the invention still further include methods of making a milk product concentrate having at least one non-reducing sugar. The methods include the steps of providing a milk product comprising a reducing sugar, and filtering the milk product to produce a retentate comprising the milk product concentrate. The methods may also include mixing oxygen into the retentate, and adding an oxidoreductase enzyme to the retentate to oxidize at least a portion of the reducing sugar to the non-reducing sugar.

Embodiments of the invention also include methods of making a milk product concentrate comprising at least one non-reducing sugar, where the methods include providing a milk product comprising a reducing sugar, filtering the milk product to produce a retentate comprising the milk product concentrate. The methods also include maintaining a pH of the retentate at about 5.5 or more by adding a buffer compound to the retentate, and adding an oxidoreductase enzyme to the retentate to oxidize at least a portion of the reducing sugar to the non-reducing sugar.

Embodiments of the invention also further include methods of making an aldobionate product, where the methods include separating a milk product into a permeate and retentate, mixing oxygen into the permeate, and oxidizing at least a portion of reducing sugar in the permeate to the aldobionate product by adding oxidoreductase enzymes to the permeate. The methods may also include drying the permeate to form a powdered composition that includes the aldobionate product.

Embodiments of the invention still also include methods of making an aldobionate product, where the methods include separating a milk product into a permeate and retentate, adding a buffer compound to the permeate to maintain a pH of the permeate at about 5.5 or more, and oxidizing at least a portion of reducing sugar in the permeate to the aldobionate product by adding oxidoreductase enzymes to the permeate. The methods may also include drying the permeate to form a powdered composition that includes the aldobionate product.

Embodiments of the invention also include processes of making an aldobionate product, where the processes include crystallizing at least a portion of a reducing sugar in a milk product to form a mixture of crystallized reducing sugar and a delactose permeate, and adding an oxidoreductase enzyme to the crystallized reducing sugar to convert at least a portion of the crystallized sugar to the aldobionate product. The processes may also include drying the aldobionate product to form a powder.

Embodiments of the invention further include processes of making an aldobionate product, where the processes include crystallizing at least a portion of a reducing sugar in a milk product to form a mixture of crystallized reducing sugar and a delactose permeate comprising residual reducing sugar, and adding an oxidoreductase enzyme to the delactose permeate to convert at least a portion of the residual reducing sugar to the aldobionate product. The processes further include drying the aldobionate product to form a powder.

Embodiments of the invention also include methods of making cheese, where the methods include converting raw milk into a mixture of curds and whey, and separating the curds from the whey, wherein the curds are used to make the cheese. The methods also include mixing oxygen into the whey while adding an oxidoreductase enzyme to the whey to oxidize a reducing sugar to an aldobionate product, and adding the aldobionate product to the cheese.

Embodiments of the invention still further include methods of making nonfat milk that includes a lactobionate product. The methods include separating raw milk into a fat portion and skim milk, mixing oxygen into the skim milk, and adding an oxidoreductase enzyme to the skim milk to oxidize lactose to the lactobionate product.

Embodiments of the invention additionally include processes of making a cheese. The processes include mixing oxygen and an oxidoreductase enzyme with a milk product to form a mixture comprising an aldobionate product. The mixture is combined with a cheese precursor to make an admixture, and the admixture is processed to form the cheese.

Embodiments of the invention also additionally include methods of cooking a foodstuff in fat or oil that reduces absorption of the fat or oil by the foodstuff. The methods include providing a foodstuff coated with a whey composition comprising a whey protein and an oxidoreductase enzyme, where the whey protein includes one or more proteins present in, or derived from, whey, and heating the coated foodstuff in the fat or oil, where the whey composition forms a film on the foodstuff to reduce the absorption of the fat or oil by the coated foodstuff relative to a corresponding uncoated foodstuff.

Embodiments of the invention still additionally include foodstuff compositions. The compositions may include an oxidoreductase enzyme and a catalase enzyme, where the enzymes create a sugar oxidization cycle where the oxidoreductase enzyme oxidizes a reducing sugar to a lactone, and a hydrogen peroxide that is converted by the catalase into oxygen ($O_2$) and water. The oxygen generated by the catalase may be used to further the reaction catalyzed by the oxidoreductase to remove the reducing sugar from the foodstuff composition, and the sugar oxidization cycle may continue until all the reducing sugar in the foodstuff has been converted into the aldobionic acid.

Additional features and advantages are set forth in part in the description that follows, and in part will become apparent to those skilled in the art upon examination of the specification or may be learned by the practice. The features and advantages may be realized and attained by means of the instrumentalities, combinations, and methods described in the specification.

DETAILED DESCRIPTION

I. Definitions

Figure 1:
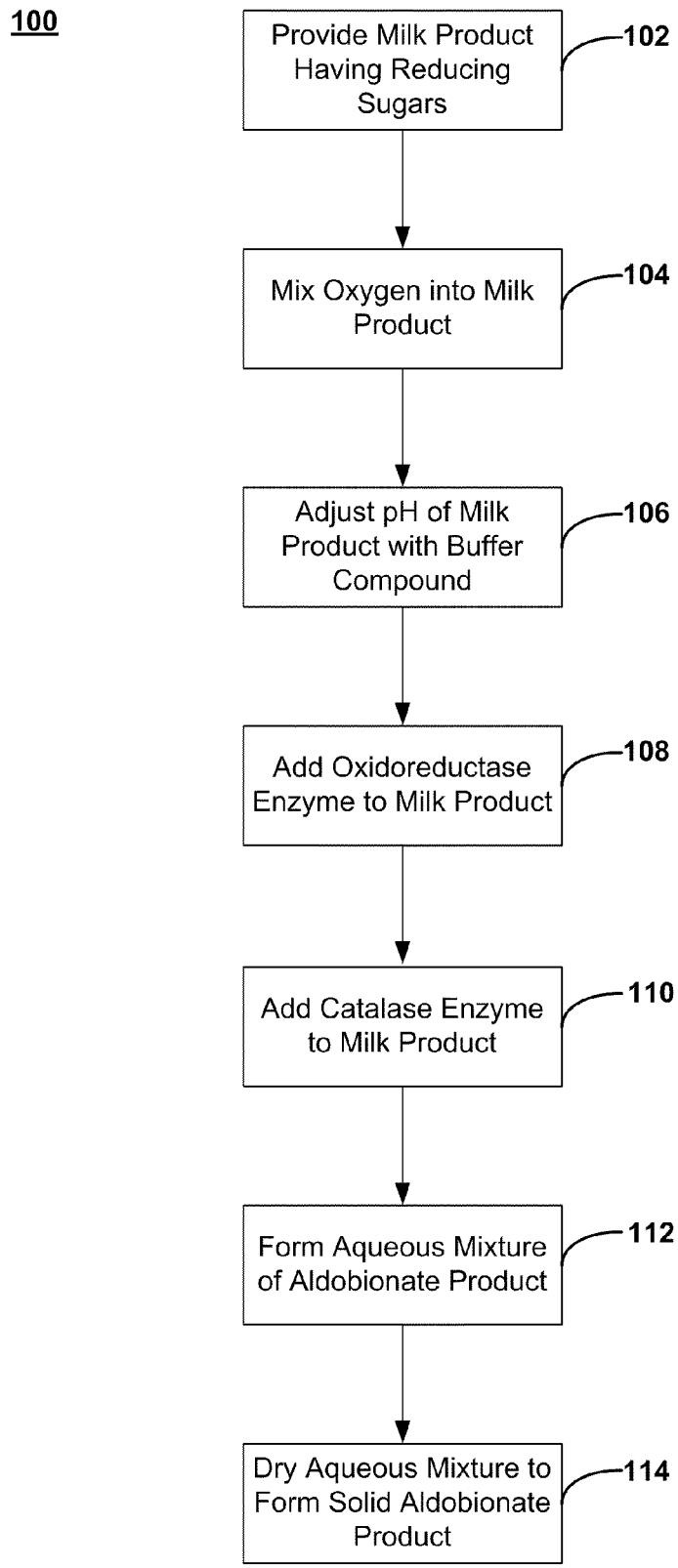
FIG. 1 is a flowchart illustrating an embodiment of a method 100 of producing aldobionate products from a milk product that contains reducing sugars.

The terms used herein have the meaning commonly understood by a person of skill in the art, as exemplified by the following definitions that are provided for some of the most commonly used terms in the application. For a definition of terms concerning whey and related products, see also, 21 CFR §184.1979, §184.1979(a), §184.1979(b), and §184.1979(c) from the Apr. 1, 2000 edition, which sections are incorporated herein by reference in their entirety for all purposes.

The term "milk product" refers to products that include whole milk, skim milk, cheese, whey, whey retentate, milk retentate, permeate, lactose, and delactose permeate, among other products.

The term "aldobionate product" refers to aldobionic acids and an aldobionate salts. These may include, for example, aldobionate salts such as sodium aldobionate, a calcium aldobionate, an ammonium lactobionate, a magnesium aldobionate, and a potassium aldobionate. Aldobionate products may also include lactobionate whey and a lactobionate nonfat milk.

The term "lactose" refers to the primary carbohydrate of the milk of most mammals is lactose (4-O-b-D-galactopyranosyl-D-glucopyranose), commonly called milk sugar.

The term "delactose permeate" generally refers to the by-product of lactose production obtained by removing a substantial portion of reducing sugars leaving delactose permeate containing reducing sugars, minerals, a minor amount of protein, and other components.

The term "reducing sugars" refer to sugars which contain a ketone or aldehyde group allowing the sugar to act as a reducing agent. Examples of reducing sugars include D-glucose, D-galactose, maltose, cellobiose, lactose, D-mannose, D-fructose, and D-xylose, among other reducing sugars. "Non-reducing sugars" refer to sugars having their anomeric carbons part of an acetal (not hemi-acetal) functional group. Sucrose is an example of a non-reducing sugar.

The term "oxidoreductase enzyme" refers to enzymes that catalyze the reaction between a reducing sugar and oxygen ($O_2$) to form a lactone and hydrogen peroxide. In aqueous environments, the lactones may hydrolyze over time to their corresponding aldobionic acids. Examples of oxidoreductase enzymes include hexose oxidase (i.e., D-hexose:oxygen 1-oxidoreductase), glucose oxidase, galactose oxidase, pyranose oxidase, and lactose oxidase, among others. The enzyme may be made by fermenting yeast strains that have been modified to include the oxidoreductase encoding gene. For example, hexose oxidase may be produced by fermentation of a selected strain of the yeast *Hansenula polymorpha* modified with the hexose oxidase encoding gene isolated from the algae *Chondrus crispus*.

The term "reducing sugar" refers to sugars (e.g., mono- and oligosaccharides) having an unsubstituted anomeric center. Examples of reducing sugars include D-glucose, D-galactose, maltose, cellobiose, lactose, D-mannose, D-fructose, and D-xylose, among other reducing sugars.

The term "catalase enzyme" refers to enzymes that catalyze the conversion of hydrogen peroxide to oxygen and water.

The term "effective amount" when used with reference to the oxidoreductase refers generally to an amount that is sufficient to prevent undesired browning of a ingredient or product (e.g., a food product or foodstuff such as cheese or a cheese-containing foodstuff). The term thus refers to an amount of oxidoreductase enzyme sufficient to convert reducing sugar in the cheese to a sufficiently low concentration such that there is negligible reaction between the remaining reducing sugar and protein in the cheese. Typically, this means that there is sufficient enzyme to lower the reducing sugar concentration to less than about 0.01 wt. %. In other instances, the reducing sugar concentration is lowered to substantially undetectable levels or is free of reducing sugar. An effective amount also refers to an amount sufficient to prevent cheese from developing a burnt appearance (e.g., whereby the melted cheese no longer has a brown appearance but becomes darker, or even black). Typically, an effective amount of oxidoreductase enzyme is about 0.025 to about 0.15 units per gram of food (e.g., cheese).

The term "cheese" as used herein refers broadly to all types of cheeses including, for example, cheeses as defined under the CODEX general Standard for Cheese and as defined under various state and national regulatory bodies. Exemplary classes of cheeses include, but are not limited to, firm/semi-hard cheeses, soft cheeses, analog cheeses, blended cheeses, and pasta filata cheeses, among other types of cheeses.

The term "firm/semi-hard cheese" includes cheeses having a percentage moisture on a fat-free basis (MFFB) of between 54% and 69%. Examples of firm/semi-hard cheeses include Colby, Havarti, Monterey Jack, Gorgonzola, Gouda, Cheshire, and Munster, low-moisture Mozzarella, and part-skim Mozzarella, among others.

The term "soft cheese" includes cheeses having a MFFB of greater than 67%. Examples of soft cheeses include standard Mozzarella, among others.

The term "analog cheese" includes cheeses in which the milk fat and/or a protein source is substituted with a source that is not native to milk.

The term "blended cheese" includes cheeses made from blends of soft or firm/semi-hard cheese with analog cheese. Conventional methods of preparing blended cheeses include blending raw ingredients for an analog cheese with a soft or firm/semi-hard cheese curd, or reworking a soft or firm/semi-hard cheese.

The term "pasta filata cheese" includes soft or firm/semi-hard cheeses made by a process in which a cheese curd is heated and kneaded to improve the stretchability or stringiness of the final cheese. This process is sometimes referred to as the pasta filata process of manufacturing a cheese.

Examples of pasta filata cheeses include mozzarella, provolone, Mexican style, scamorze, and pizza cheese.

The term "cheese precursor" as used herein refers broadly to any ingredient that is used to prepare a cheese curd, mixtures of such ingredients and subsequent processed forms of the cheese curd into a cheese. Examples of cheese precursors that are ingredients include, but are not limited to, unpasteurized milk (sometimes referred to in the industry as "raw milk"), the growth medium and bacteria used in the cheese making process (sometimes referred to in the industry as "starter"), and cream. Mixtures of such ingredients are also included. One specific example of such mixtures is "vat liquid", which is a term used to refer to a combination of pasteurized milk, starter and cream. The term also includes coagulum, cheese curd, and processed cheese curd (e.g., curd that has been heated and/or stretched to form a homogeneous mass of soft or firm/semi-hard cheese), but does not include the final cheese product.

The term "curd precursor" refers to an ingredient, mixture or composition used in the manufacture of cheese curd that exists or is formed prior to formation of the cheese curd. The term thus includes, for example, raw milk, starter, cream, cheese vat and coagulum.

The terms "protein" and "polypeptide" are used interchangeably herein. The terms broadly refer to polymers of amino acids, optionally including amino acid analogues, as well as salts of such polymers.

"Whey" generally refers to the liquid substance that is obtained by separating the coagulum from milk, cream, or skim milk in cheesemaking. The two major protein components in whey are α-lactalbumin and β-lactoglobulin. Other major components are lactose and various minerals. "Acid whey" generally refers to whey obtained from a process in which a significant amount of the lactose has been converted to lactic acid, or from the curd formation by direct acidification of milk. "Sweet whey" generally refers to whey obtained from a procedure in which there is insignificant conversion of lactose to lactic acid. "Concentrated whey" is the liquid substance obtained by the partial removal of water from whey, while leaving all other constituents in the same relative proportion. "Dry or dried whey" generally refers to the dry substance obtained by removal of water from whey, while leaving all other constituents in the same relative proportion as in whey.

A "whey protein concentrate" generally refers to a dry substance obtained by remove of water, lactose, and minerals from whey, in which the protein is concentrated to about 35% to about 90% wt.

The term "thermally coagulating protein" as used herein refers to proteins that coagulate to form a film or gel once heated to a sufficiently high temperature such that the proteins denature.

"Reduced lactose whey" refers to the substance obtained by the removal of lactose from whey. The protein content is 16-24% by weight.

"Reduced minerals whey" generally refers to the substance obtained by the removal of the minerals from whey, such that the resulting product contains less than 7 percent ash. The protein concentration is 10-24% by weight.

"High gel whey" is whey to which calcium has been added in a sufficient amount to promote coagulation of whey protein to form a film or gel.

"Hydrolyzed whey" is whey in which the protein present in the whey has been at least partially hydrolyzed using enzymes.

A "coat" or a "coating" generally refers to one or more layers of composition (e.g., a whey composition) that is applied to an exterior surface of a foodstuff. A coating typically does not extend into the whole foodstuff, but instead resides relatively close to the surface of the foodstuff. This, however, is not required; in some instances, the coating can extend throughout the foodstuff. A coating may be applied to a limited portion of the foodstuff (e.g., one side), but can also be applied such that the entire exterior surface of the foodstuff is coated (e.g., when the foodstuff is submerged into the coating composition).

The terms "food", "foodstuff", "food product" and other related terms as used herein refer to essentially any type of food item that is compatible with the coating and heating processes of the disclosed methods. Suitable foods include, but are not limited to, cereal-based products, cheese, poultry, beef, pork, seafood, potatoes (e.g., potato chips, French fries, hash browns, potato strings, etc.), vegetables (e.g., zucchini, peppers (e.g., jalapenos), cauliflower, etc.), mushrooms, fruit, candy and nuts. Diverse types of cereal-based products can be utilized. Exemplary food products of this type include pizza dough, burritos, dough-enrobed sandwiches, hand-held foods, bread dough, bagel dough, scones, cereals, pastries, and grain-based snack foods (e.g., crackers and pretzels). Hand-held foods include, for example, burritos, sandwiches (including pocket sandwiches) and pitas.

"Fat" is a water-insoluble material derived from plants or animals and is composed primarily of a mixture of glycerol esters (e.g., triglycerides). At room temperature, fats typically exist as semi-solids.

An "oil" is a fat in liquid form. Because during cooking (e.g., frying or baking) a fat is present as a liquid, the term oil can appropriately be used interchangeably with the term fat (see, e.g., Robert S. Igoe, Dictionary of Food Ingredients, 2nd ed., 1989).

II. Overview

Food ingredients and food products are described that have decreased amounts of reducing sugars, which makes them less susceptible to Maillard browning. The reducing sugars may be removed by an oxidoreductase enzyme that catalyzes the oxidation of the sugar into a lactone (i.e., a cyclic ester), which may undergo subsequent hydrolysis to the corresponding aldobionic acid. For many oxidoreductases, the catalytic oxidation of a reducing sugar is accompanied by formation of hydrogen peroxide ($H_2O_2$), which can act as a peroxide preservative in the food.

Cheeses containing oxidoreductase enzymes are one type of food that is provided. One or more oxidoreductase enzyme may be added during the cheesemaking process, or mixed in after the cheese is made to reduce the content of reducing sugars (e.g., lactose) in the cheese. The lowered concentration of reducing sugars results in less Maillard browning (which requires the presence of reducing sugars) as the cheese is cooked, for example, on pasta or pizza dough. A variety of foodstuffs containing such cheeses are also provided.

Food ingredients may include coating compositions for foods that reduce fat and/or oil absorption in the food during cooking (e.g., deep fat frying). The coating compositions include an oxidoreductase enzyme that catalyze the oxidation of one or more reducing sugars to reduce browning during cooking, and generate peroxide preservatives that slow mold growth and lengthen the self-life of the coated food. The coated foods may include coated cheese (e.g., fried mozzarella cheese sticks) and the coating composition may include whey proteins generated from the cheese making process.

Additional food ingredients include treated milk powder that can be added to a cheese to fortify its protein content. Concentrated and powdered dairy milk are rich in proteins, but also rich in reducing sugars such as lactose. Oxidoreductase enzymes may be added to the milk to decrease the sugar concentration while maintaining high levels of protein. The resulting protein-rich, reduced-sugar milk concentrate or powder may be added to other ingredients to make the protein fortified cheese. Fortified cheeses can be made that have a low concentration of reducing sugars and experience less browning when cooked.

Methods of treating food byproducts with oxidoreductase enzymes to produce useful materials for non-food industries are also described. In many instances, the economic demand for an aldobionic acid is much higher than its corresponding reducing sugar. Reducing sugars, produced as byproducts of a food making process, with oxidoreductase enzymes may be oxidized to convert the sugars into lactones, which in turn may be hydrolyzed into their corresponding aldobionic acids. For example, in cheese making processes a lactose-rich whey component is separated from the curds. The whey component may then be filtered to separate a retentate that is mostly whey protein from a liquid permeate that includes lactose and minerals. Oxidoreductase enzymes may be added to the permeate to covert the lactose into lactobionic acid by way of a lactolactone. The lactobionic acid may then be dehydrated by, for example, a spray drying process to form a powder.

III. Methods of Preparing Cheeses

A. General Considerations

The cheese making methods that are provided can accommodate essentially any method of cheese manufacturing. At some step during the cheese manufacturing process, or after the cheese is made, one or more oxidoreductase enzymes are added. The cheese making techniques used in these processes can be utilized to prepare virtually any type of cheese, including, but not limited to, soft cheeses, firm/semi-hard cheeses, natural cheeses, pasta filita cheeses, analog cheeses, and blended cheeses, among other kinds of cheeses.

The oxidoreductase enzymes may be added to a cheese or cheese precursor in a variety of ways including spraying the enzyme onto the precursor or the formed cheese, injecting the enzyme into the precursor or the formed cheese, dipping the precursor or the formed cheese into a solution containing the enzyme, mixing the precursor or the formed cheese with a dry powder form of the enzyme, and mixing the precursor or the formed cheese with a solution containing the enzyme, among other ways. The oxidoreductase enzyme is typically included in an amount effective to control browning in the final cheese product. Typically, about 0.025 to about 0.15 units of oxidoreductase enzyme are added per gram of cheese (e.g., 0.025-0.05, 0.05-0.10 or 0.10-0.15 unit/g of cheese).

In addition to the oxidoreductase enzymes, hydrogen peroxide converting enzymes that convert hydrogen peroxide into a less reactive form may also be added at some point during or following the cheesemaking process. An example of a suitable hydrogen peroxide converting enzyme is catalase, which catalyzes the breakdown of hydrogen peroxide (produced, for example, by the oxidoreductase enzymes) into water and oxygen ($O_2$).

Some cheesemaking methods described herein include forming a coagulum of curd and whey from milk, and processing the curd into a cheese. Other methods include the formation of a slurry that may be processed into a cheese. Still other techniques include forming an admixture from the combination of a slurry with additional ingredients, and processing the admixture into a cheese. Oxidoreductase enzymes may be added at any point during a cheesemaking technique, including times prior to, during, and/or after the formation of a coagulum, slurry, or admixture. The oxidoreductase enzymes may also be added to the cheese after it has been made by, for example, spraying or otherwise coating the cheese with the enzyme. Oxidoreductase enzymes may also be added after the cheese is processed into its final form (e.g., sliced, shredded, grated, block, sectioned, etc.). For example, the enzyme may be applied to shredded cheese along with an anticaking agent that prevents the cheese from clumping. Additional details for some of these cheesemaking techniques will now be given.

B. Exemplary Methods of Preparing Cheeses

Methods of preparing some traditional cheeses may include acidifying milk (e.g., pasteurized cow's or buffalo milk) to convert it into cheese milk. The cheese milk may then be coagulated to form a coagulum that includes cheese curds and whey. The whey may be drained away from the coagulum to leave the cheese curds. The curds may then be placed into a mold, where they ripen into the cheese. The oxidoreductase enzymes may be added at any point, including being added to the unacidified or acidified milk, the coagulum, the cheese curds, and/or the ripened cheese, among other steps of the cheesemaking technique.

For example, the acidification of the milk may be performed either microbially, directly, or by a combination of microbial and direct acidification. Microbial acidification is accomplished by the addition of a starter culture of one or more lactic acid-producing bacteria to the milk, and then allowing the bacteria to grow and multiply, while direct acidification is accomplished by the addition of a GRAS acid, such as, acetic acid (e.g., as vinegar), phosphoric acid, citric acid, lactic acid, hydrochloric acid, sulfuric acid, or glucono-delta-lactone (GdL), lactobionic acid to the milk. Oxidoreductase enzyme may be added during the acidification step to increase the oxidation and hydrolysis of reducing sugars like lactose to lactobionic acid.

Oxidoreductase enzymes may also be added following acidification, when the cheese milk is coagulating to form a coagulum that consists of cheese curd and whey. The oxidoreductase enzymes may be added with rennet or other suitable enzyme(s) that are commonly added to the milk to enhance coagulation activity. The oxidoreductase enzymes may also be added after the coagulum is cut and the whey drained off to obtain the cheese curd.

Oxidoreductase enzymes may also be included at various stages in the preparation of cheeses in which the production process involves heating, kneading, and/or stretching the cheese curd in a mixer to form a homogeneous heated mass of cheese that is subsequently processed into a final form. Examples of cheeses prepared according to such methods include, but are not limited to, soft and firm/semi-hard cheeses (e.g., pasta filata and mozzarella). In some methods involving a heating and kneading step, the curd and/or heated cheese mass may be mixed with additional liquid or dry ingredients. The cheese may then be shaped by an extruder and cooled in a tank of cold brine, and ingredients may also be added as the cheese is being shaped by the extruder and/or after the cheese is cooled by the brine. Cheesemaking techniques that include heating, kneading and/or stretching cheese curd are described in co-assigned U.S. Pat. No. 5,902,625, titled "Process Of Making A Soft Or Semi-Soft Fibrous Cheese", filed Oct. 18, 1996, the entire contents of which are herein incorporated by this reference for all purposes. The oxidoreductase enzymes may be added at any point, including the steps of heating, kneading, and/or stretching the cheese curd, and/or during the shaping and cooling of the cheese, among other steps. The oxidoreductase enzymes may be added separately, or may be part of a mixture that includes one or more other ingredients.

Oxidoreductases can also be introduced in cheesemaking techniques in which a cheese curd and other ingredients are initially introduced into a grinder that reduces the sizes of the curd and incorporates the ingredients into the curd and the resulting impregnated curd transferred to a mixer where the mixture may be heated, kneaded and/or stretched into the cheese. In some methods, additional ingredients may be added after this heating and kneading process. The cheese may then be shaped with an extruder and cooled in brine. Examples of this approach are discussed in co-assigned U.S. patent application Ser. No. 10/300,019, titled "Process of Making A Homogenous Cheese", filed Nov. 20, 2002, the entire contents of which are herein incorporated by this reference for all purposes. Oxidoreductase enzymes may be added at any point in processes of this type, including during the grinding and/or mixing steps of these techniques.

Oxidoreductases can also be incorporated into cheese manufacturing processes that utilize a slurry. In methods of this type, the slurry may include certain ingredients that one seeks to introduce into the final cheese product. As described further below, the ingredients included in the slurry can include cheese curd, various analog cheese ingredients and various other ingredients such as those listed below.

In some cheese manufacturing methods, the slurry may be prepared separately and then mixed with a cheese precursor, while in other techniques the cheese curd may be a component of the slurry. An example of preparing a slurry without cheese curd includes mixing the slurry ingredients in a blender and heating them in a cooker. The slurry can optionally be sheared, homogenized and/or the water content adjusted. The resulting slurry may then be mixed with a cheese precursor (e.g., a heated mass of homogenized cheese produced by heating and kneading a cheese curd) to form an admixture that may then undergo further processing to yield the final cheese product.

In other cheese manufacturing methods in which the slurry includes cheese curd, cheese curd is typically combined with an ingredient in a blender and then cooked or cooked during the blending process. In some methods of this type, the curd-containing slurry may then be processed through a shear pump and homogenizer. Other ingredients can optionally be combined with the resulting mixture in a mixer. The curd-containing slurry is then subjected to final processing to obtain the final cheese product.

In any of the slurry-based cheese manufacturing methods, oxidoreductase enzymes may be added at any point during this process, including during the formation or processing of the slurry, and/or the subsequent mixing of the slurry with a cheese precursor, for example. One specific option, for instance, is to include the oxidoreductase in the slurry itself. Another option is to add the oxidoreductase once the slurry has been combined with a cheese precursor (e.g., homogenized mass of heated cheese curd).

Further details regarding the use of slurries in the preparation of various types of cheeses are provided in U.S. patent application Ser. No. 11/121,537, filed May 3, 2005, now U.S. Pat. No. 7,585,537, entitled "Cheese and Methods of Making Such Cheese,", U.S. patent application Ser. No. 11/122,283, filed May 3, 2005, now U.S. Pat. No. 7,651,715, entitled "Blended Cheeses and Method for Making Such Cheeses,", and U.S. patent application Ser. No. 11/121,398, filed May 3, 2005, now U.S. Pat. No. 7,579,033, entitled "Methods for Making Soft or Firm/Semi-Hard Ripened and Unripened Cheese and Cheeses Prepared by Such Methods,", each of which is incorporated herein by reference in its entirety for all purposes.

C. Ingredients for Incorporation into Cheese

The oxidoreductase enzyme and/or hydrogen peroxide converting enzyme, if utilized, can be incorporated into a final cheese product as part of a mixture of other food ingredients. Some of these ingredients are ones that are commonly used in the preparation of analog cheeses. Such ingredients include, for example, oils, fats, proteins, starches, sequestrants, and/or salts. Examples of other ingredients with which the oxidoreductase enzyme can be combined include, but are not limited to, nonfat dry milk, a milk protein, an acidity regulator, an acid, an anticaking agent, an antifoaming agent, a coloring agent, an emulsifier, an enzyme preparation, a flavoring agent, a firming agent, a food protein, a gelling agent, a preservative, sequestrants, a stabilizer, a starch, a thickener, an oil, a fat, a cheese powder, a salt, a nutritional supplement, an acid, an enzyme, a neutraceutical, a carbohydrate, a vitamin, and a mineral.

IV. Cheeses

The methods that are described herein can be utilized to prepare cheeses that contain one or more, native or denatured, oxidoreductase enzymes. The oxidoreductase is present in an effective amount (e.g., about 0.025 to about 0.15 units per gram of cheese). The cheeses may have lower amounts of reducing sugars (e.g., about 0.5%, 0.1%, 0.01%, or 0.05%, or less, by weight) than similar cheeses that do not contain oxidoreductase enzymes. The cheeses may also contain hydrogen peroxide generated during the catalytic oxidation of reducing sugars in the cheese by the oxidoreductase enzymes. The cheeses may further contain a catalyze enzyme for breaking down the hydrogen peroxide into oxygen and water. Additional ingredients may also be present in the cheeses.

The soft or firm/semi-hard cheeses that are provided typically have a protein content of about 10-40 wt. %, a moisture content of about 35-65%, and a fat content of about 0-60% on a dry basis (FDB). The actual composition varies somewhat depending upon the particular type of mozzarella cheese that is to be produced. For certain soft or firm/semi-hard cheeses (mozzarella cheeses) that are provided, the milk fat content is at least 45% by weight of solids and the moisture content is about 52-60 wt. %. The low-moisture soft or firm/semi-hard cheeses (also sometimes referred to as low-moisture mozzarella cheeses) that are provided generally have a minimum milk fat content of 45% by weight of solids and a moisture content that is about 45-52 wt. %. Part skim-milk soft or firm/semi-hard ripened and unripened cheeses (also called part skim mozzarella cheeses) that are provided, in contrast, have a milk fat content that ranges from about 30-45% by weight of solids and a moisture content that is about 52-60 wt %. The low-moisture, part-skim soft or firm/semi-hard ripened and unripened cheeses (also referred to as low-moisture, part skim mozzarella cheeses) that are provided usually have a milk fat content of about 30-45% by weight of the solids and a moisture content of about 45-52 wt %. The foregoing moisture percentages are for bound plus free water, i.e., the percent of weight lost when the cheese is dried for 17 hrs±1 hr in a 100° C. oven.

The cheeses that are provided can be in a variety of different forms including blocks, loaves, Ribbons™, comminuted forms (e.g., diced or shredded forms) and other forms known in the art. The pH of the cheese generally ranges from about 5.00 to about 6.00, such as about 5.10 to about 5.90.

V. Food Products and Methods of Manufacturing Such Foodstuffs

The cheeses that are provided can be utilized in essentially any baking application that involves the use of cheese and can be incorporated into a wide variety of foodstuffs. The cheeses, for instance, can be included as an ingredient in a variety of convenience foods, including entrees, snack foods and appetizers.

The cheeses can be incorporated into the foodstuff, layered onto or in the foodstuff or used as a coating. One common use, for example, is as an exposed cheese on a pizza or as the string cheese rolled in the outer lip of a pizza crust (a so-called "stuffed crust pizza").

As those skilled in the art will recognize, the foregoing list is simply illustrative and is not intended to an exhaustive list of the types of foods that can be combined with the soft or firm/semi-hard cheeses that are provided herein.

The cheeses that are provided are suitable for use in essentially any type of cooking including convection heating, steam injection heating and microwave heating, for example. In some microwave heating applications, for example, the food product is exposed to microwave energy in an amount and for a duration sufficient to heat and melt the cheese, whereby the cheese melts to form a uniform mass of cheese. The cheeses can generally be heated in a variety of microwaves, such as microwaves having wattages of 400-1000 watts, or full power microwave ovens of 650-850 watts that are common home microwave ovens. The cheeses can be cooked over a range of cooking times such as from 0.5 to 20 minutes, or 0.5-10 minutes, or 2-5 minutes, which are the typical microwave cook times used to prepare frozen or refrigerated entrees and appetizers.

The cheeses that are disclosed herein can be combined with essentially any foodstuff using any of a variety of methods. For example, the foodstuff can be dipped in melted cheese. Alternatively, the cheese can be sprinkled or layered onto the foodstuff using conventional food processing equipment. In such processes, the cheese is typically first comminuted to form relatively small pieces of cheese or shredded cheese. Once the cheese has been combined with the foodstuff, the resulting food product can optionally be refrigerated or frozen for future sale or use.

VI. Coatings

Foodstuff coating compositions comprising aldobionate products are described. The compositions may also include one or more thermally coagulating proteins that coat foodstuffs and render them less permeable to fat and oil in a frying medium, thus reducing the amount of fat or oil absorbed by the foodstuff during cooking. Methods for preparing such foodstuffs are also described. A variety of compositions useful in coating foodstuffs are also described.

The food products, coatings and food preparation methods that are disclosed herein have value in view of the increased demand by consumers for foods that are lower in fat and oil but that have increased protein content. As described in greater detail below, one group of thermally coagulating proteins that have been found to be useful in the foodstuffs and compositions that are provided are whey proteins, including whey proteins present in fractions of whey or individual proteins that are major components of whey, such as $\alpha$-lactalbumin and $\beta$-lactoglobulin. The use of whey proteins in the coating is desirable because they have relatively neutral flavors that do not affect the taste of the foodstuff being prepared, unlike certain other proteins that can impart an undesirable flavor. It should be understood, however, that these particular proteins are exemplary and that the application is not limited to these particular proteins. The coating composition can also contain one or more other ingredients in addition to a thermally coagulating protein such as a whey protein. The composition (e.g., a whey composition) can also include, for instance, batter, breading, flavoring agents, thermal gelling agents, stabilizing agents, colors, anti-oxidants and preservatives.

Some coating compositions contain whey protein. The term "whey protein" refers to one or more proteins naturally present in or derived from whey. This means that the whey protein in the composition can be one or more proteins from any of a number of different whey protein source materials. A "whey protein source material" generally refers to sources such as whey, acid whey, sweet whey, concentrated whey, dry whey, reduced lactose whey, reduced minerals whey, whey protein concentrate, high gel whey, hydrolyzed whey, specific proteins from whey (e.g., $\alpha$-lactalbumin and $\beta$-lactoglobulin), as well as combinations of one or more of the foregoing sources and sources derived from the foregoing sources. These source materials may optionally be in concentrated, diluted, instantized or agglomerated forms, for example. A "whey composition" is a composition that comprises whey protein and optionally additional ingredients such as starch, batter, breading, flavors, texturizers, and stabilizing agents. A whey composition thus may simply be one of the foregoing whey protein source materials or a mixture of such a source material with one or more other ingredients.

Coatings are typically prepared by adjusting the whey protein concentration of a whey protein source material (e.g., by concentrating or diluting) to obtain the desired concentration of whey protein appropriate for a given application. But in some instances, certain whey protein source materials can be used directly.

So, as one illustration, a whey composition can be prepared from whey protein concentrate (e.g., 80% whey protein), typically by diluting it (e.g., with water or oil) to obtain a composition with the desired whey protein concentration. This diluted solution can optionally also be mixed with or more additional ingredients (e.g., a breading, a batter, and/or a starch).

The concentration of the thermally coagulating protein (e.g., whey protein) may be up to about 40-55% protein by weight or more, depending on the application (e.g., about 2% to about 55% by weight). At higher protein levels, foodstuffs cooked in oil and fat have been found to exhibit good color characteristics (e.g., browning) and texture (e.g., the crispiness desired in food cooked in fat or oil). On the other hand, some foodstuffs have comparatively low protein concentrations (e.g., less than about 2%), for example when specific types of whey protein sources are utilized (e.g., reduced mineral whey, high gel whey and hydrolyzed whey).

The oxidoreductase enzymes help reduce the relatively high sugar contents in many whey protein based coatings, which reduces the browning of the foodstuff (i.e., the food become too dark in color) during cooking. The peroxide products generated by the enzyme also give the coating preservative properties that extend the freshness of the coated foodstuff.

When the compositions that are provided are used to coat foodstuffs, significant reductions in fat or oil absorption by the foodstuff can be obtained. This result is achieved because the coatings once heated act to decrease the permeability of the foodstuff to oil and fat. For example, with the coatings that are disclosed herein fat or oil absorption into the foodstuff can be reduced by at least 5%, 10% or 15% relative to a corresponding foodstuff of the same type that is not coated with the thermally coagulating protein (e.g., whey composition). In other instances, fat or oil absorption is reduced by at least 20% or 25%. With still other foodstuffs, fat or oil absorption is reduced by at least 30%, 35% or more.

Without intending to be bound by any theory, the ability of the disclosed compositions to inhibit fat and oil absorption is thought to be due to the inclusion of thermally coagulating proteins in the composition. With proteins of this type, the gel or film is formed after at least a part of the protein has been heat denatured. Gel formation typically involves a number of consecutive reactions: (1) protein molecules become denatured; (2) denatured molecules aggregate to form (roughly spherical or elongated) particles; and (3) these particles then aggregate further to form a space-filling network. Thus, for film formation, the protein should be soluble, capable of rapidly diffusing to an oil-water interface, where it can reorient, unfold to some degree, and then spread, with one or more segments occupying the non-polar oil phase. Extensive interactions should occur among contiguous molecules, that is, intermolecular interactions, to form a coherent film. The coatings so formed are thus able to reduce the permeability of foodstuffs to fat and oil.

Exemplary thermally coagulating proteins include, but are not limited to, whey protein, egg albumin, myosin, casein(s) and soy protein.

Certain food preparation methods that are provided herein generally involve providing a foodstuff and then applying a coating to the foodstuff. The coating typically contains aldobionate products and thermally coagulating protein. Alternatively, the aldobionate products may be added after the coating is deposited on the foodstuff. The thermally coagulating protein typically comprises at least 2, 3, 4 or 5% of the coating composition by weight. The protein concentration in the coating composition typically does not exceed 40, 45, 50 or 55%, by weight. So a typical protein concentration is 2-55% by weight. As described in greater detail below, the particular protein concentration level utilized depends in part upon the mode by which the composition is applied to the foodstuff and whether other ingredients (e.g., batter or breading) are part of the coating composition.

Coatings are typically prepared by adjusting the whey protein concentration of a whey protein source material (e.g., by concentrating or diluting) to obtain the desired concentration of whey protein appropriate for a given application. The concentration of aldobionate products in the coating may also be adjusted. In some instances, certain whey protein source materials can be used directly.

A "whey protein source material" generally refers to sources such as whey, acid whey, sweet whey, concentrated whey, dry whey, reduced lactose whey, reduced minerals whey, whey protein concentrate, high gel whey, hydrolyzed whey, specific proteins from whey (e.g., α-lactalbumin and β-lactoglobulin), as well as combinations of one or more of the foregoing sources and sources derived from the foregoing sources. These source materials may optionally be in concentrated, diluted, instantized or agglomerated forms, for example. A "whey composition" is a composition that comprises whey protein and optionally additional ingredients such as starch, batter, breading, flavors, texturizers, and stabilizing agents. A whey composition thus may simply be one of the foregoing whey protein source materials or a mixture of such a source material with one or more other ingredients.

A whey composition can be prepared from whey protein concentrate (e.g., 80% whey protein), typically by diluting it (e.g., with water or oil) to obtain a composition with the desired whey protein concentration. This diluted solution can optionally also be mixed with one or more additional ingredients (e.g., a breading, a batter, and/or a starch). Further illustrative examples of different whey coating compositions for specific application modes are described in greater detail below.

These coatings can be applied to a variety of different foodstuffs. Initial preparation of a foodstuff to be coated is according to methods that are generally known in the food industry to be appropriate for the particular type of foodstuff being coated. So, for example, foodstuffs are washed, cut to size and/or ingredients for the foodstuff combined to prepare the food substrate to be coated. Optionally, the water content of the food can be adjusted to a desired range and/or the food parfried (i.e., partially cooked) prior to applying the coating.

The composition can be coated onto the foodstuff using essentially any technique utilized in the art. Examples of suitable approaches include spraying, dipping, basting and brushing. The foodstuff can optionally be battered and/or breaded. This can be done before, during or after application of the coating composition to the foodstuff. So, for example, a foodstuff can first be coated with the coating composition and then the batter and/or breading applied. Alternatively, a layer of batter and/or breading is applied, the coating composition is then applied, and finally another layer of batter and/or breading is applied. Such methods typically involve first applying a layer of batter to the substrate, then the coating composition and finally a breading layer. Yet another option is to apply the batter and/or breading and then apply the coating composition. As noted above, the coating composition itself can include a batter and/or breading. In which case, the coating composition and batter and/or breading are applied simultaneously.

After the coating composition has been applied, the coated foodstuff is optionally allowed to dry and/or sit to allow excess coating composition to be removed and for the coating composition to be absorbed. The coated foodstuff can then optionally be frozen or par-fried and stored for later use.

Once the foodstuff is to be served, it may be heated to a temperature that is sufficiently hot to cause the protein in the coat to denature. As described above, the resulting denatured protein then spreads to form a film that reduces the porosity of the foodstuff and restricts absorption of oil and fat by the underlying foodstuff. Any heating procedure utilized in the cooking industry can be utilized to heat the substrate. Typically, heating is accomplished in the presence of a fat or oil. Examples of suitable heating options include, but are not limited to, frying (including deep fat frying), heating with a radiation or convection oven, microwaving, steaming, high pressure extruding and heating on a rotating drum. Foodstuff coatings and coating techniques are described in co-assigned U.S. Provisional Patent App. No. 60/515,917, filed Oct. 29, 2003, and entitled "Coated Food Products and Methods of Producing Coated Food Products with Reduced Permeability to Fat and Oil", the entire contents of which are herein incorporated by this reference for all purposes.

VII. Methods of Making Aldobionate Products

Aldobionate products may be produced (for both food and non-food industries) through the treatment of milk products with oxidoreductase enzymes. The milk products include reducing sugars that are catalytically converted into the aldobionate products by the enzymatic action of the oxidoreductase enzymes. The oxidoreductase enzymes may include hexose oxidase, glucose oxidase, galactose oxidase, pyranose oxidase, and lactose oxidase, among other oxidase enzymes. Milk products having reducing sugars that may be oxidized by the enzymes may include whole milk, skim milk, cheese, whey, whey retentate, milk retentate, permeate, lactose, and delactose permeate. The aldobionate products produced by the enzymes may include aldobionic acids and aldobionate salts, including sodium aldobionate, calcium aldobionate, ammonium aldobionate, magnesium aldobionate, and potassium aldobionate, among others. The aldobionate products also include lactobionic acid and lactobionate salts, as well as non-reducing sugars like lactolactones.

FIG. 1 shows a flowchart illustrating an embodiment of a method 100 of producing aldobionate products from a milk product that contains reducing sugars. The method 100 starts by providing a milk product that contains reducing sugars 102, and mixing oxygen into the milk product 104. The oxygen is supplied to facilitate a more complete and uniform catalysis of the reducing sugars into aldobionate products throughout the milk product. Without this mixing, oxidoreductase catalysis is often more active around the surfaces of the milk product in contact with the surrounding air, and least active at points furthest removed from these surfaces. Techniques for mixing the oxygen into the milk product may include injecting an oxygen source (e.g., air, purified oxygen, etc.) into the milk product, bubbling oxygen through the milk product (when the milk product is a liquid or aqueous mixture), and/or mixing or agitating the milk product in an environment containing oxygen, among other techniques.

In addition to (or in lieu of) mixing oxygen into the milk product, the pH of the milk product may be adjusted with a buffer compound 106. The aldobionate products of the oxidoreductase catalysis include aldobionic acids that can lower the pH of the surrounding milk product. In some instances, the pH can drop to a point where the catalysis reaction is no longer favored, and/or other undesirable conditions start to develop (e.g., the milk product tastes too sour, etc.). The buffer compound is added to adjust and/or maintain the pH of the milk product reaction environment in a desired range (e.g., a pH of about 5.5 or greater). Buffer compounds may include calcium hydroxide, calcium carbonate, ammonium carbonate, sodium carbonate, potassium hydroxide, magnesium carbonate, magnesium hydroxide, ammonium hydroxide, and sodium hydroxide, among other buffer compounds.

The oxidoreductase enzyme is added to the milk product 108 to start the catalytic conversion of the reducing sugars. The amount of oxidoreductase enzyme provided may be about 0.1 gram to about 20 grams, by weight, per kilogram of the reducing sugar in the milk product. The oxidoreductase catalysis starts with the reducing sugar, water, and oxygen being catalytic converted into a lactone and hydrogen peroxide. The lactone may be subsequently hydrolyzed to form an aldobionic acid, and the reactive peroxide may be involved in a variety of reactions. A catalase enzyme may be added to the milk product 110 to convert the peroxide by product into molecular oxygen and water. The oxygen produced by the catalase enzyme can provide an additional source of oxygen for the oxidoreductase catalysis, creating a self-sustaining catalytic cycle for converting the reducing sugars to aldobionate products.

The catalytic activity of the oxidoreductase enzymes convert the milk product into an aqueous mixture of aldobionate product 112. In some embodiments, the oxidoreductase enzymes convert all the reducing sugars in the milk product to aldobionate products, while in other embodiments less than all the reducing sugars are converted, leaving an aqueous mixture that includes both aldobionate product and residual reducing sugars. The aqueous mixture may be dried to form a solid aldobionate product 114, that may be used as a food additive, and/or non-food related uses (e.g., cosmetics, detergents, organ transplant preservation compound, etc.). Drying techniques may include spraying the aqueous mixture into a heated area, where moisture is evaporated from the aldobionate product, and a dry powder is formed.

Figure 2:
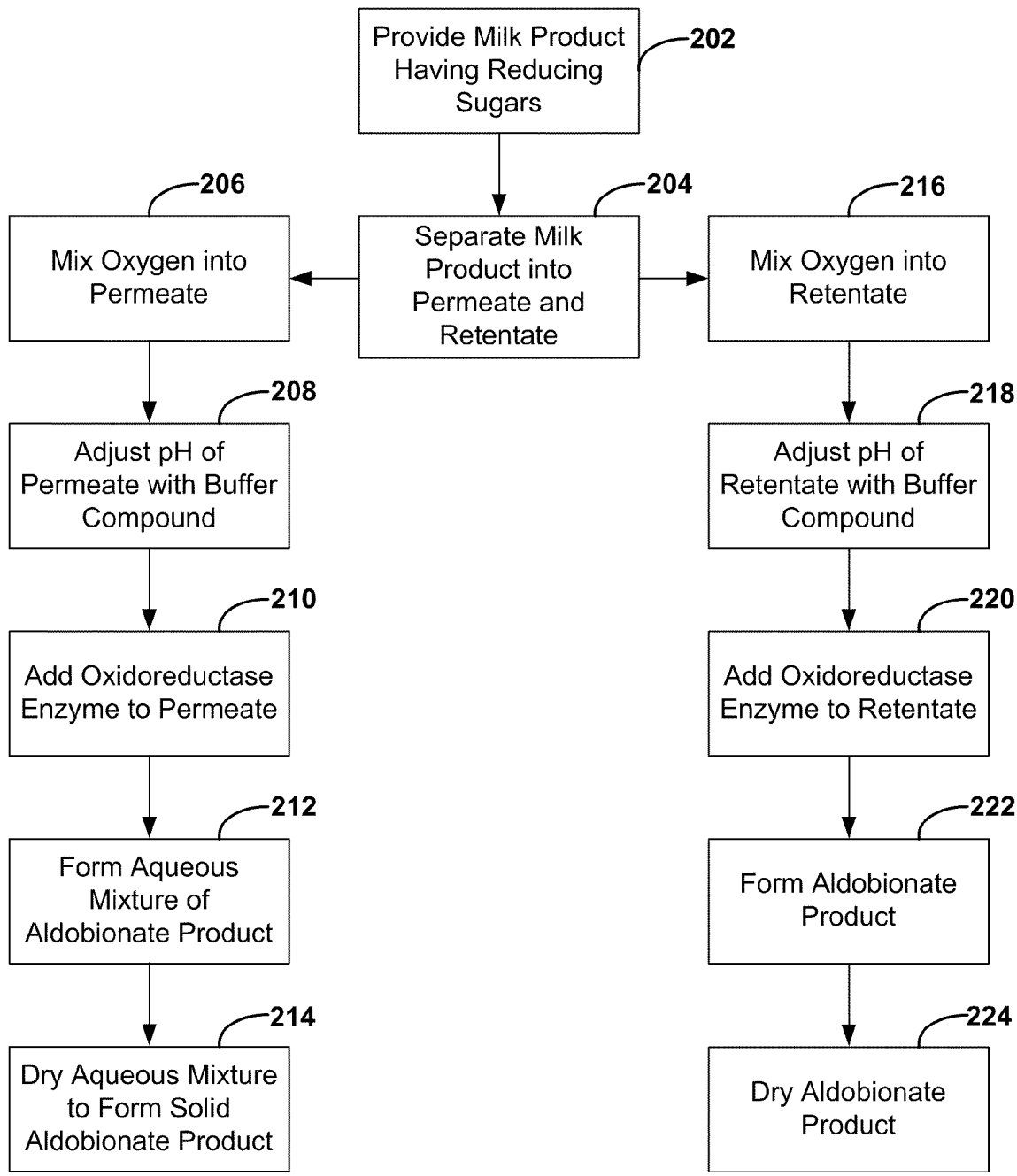
FIG. 2 is a flowchart illustrating another embodiment of a method 200 of making aldobionate products.

Referring now to FIG. 2, a flowchart illustrating another embodiment of a method 200 of making aldobionate products is shown. Method 200 includes providing a milk product that has a reducing sugar 202. The milk product may be separated into permeate and a retentate 204. For example, when the milk product is raw milk the permeate may include reducing sugars and minerals, and the retentate may include milk proteins, reducing sugars, minerals and milk fats. In another example, when the milk product is raw whey from the separation of curds and whey, the permeate is whey permeate (which may include reducing sugars and minerals) and the retentate is whey protein concentrate (which may also include reducing sugars).

Both the milk product permeate and retentate may be treated to convert at least a portion of the reducing sugars into aldobionate products (e.g., non-reducing sugars, etc.). Oxygen may be mixed into the permeate 206 and/or the pH of the permeate may be adjusted by addition of a buffer compound 208. Oxidoreductase enzyme is added to the permeate 210 to convert reducing sugars and form an aqueous mixture with the aldobionate products 212. The aqueous mixture may be dried to form a solid (e.g., powdered) aldobionate product 214.

A similar oxidoreductase treatment may be performed on the retentate: Oxygen may be mixed (e.g. injected) into the retentate 216 and/or the pH of the retentate may be adjusted with the help of a buffer compound 218. Oxidoreductase enzymes may be added to the retentate 220 to convert reducing sugars present into an aldobionate product 222. The aldobionate product containing retentate may the be dried to form a dry aldobionate product 224.

Figure 3:
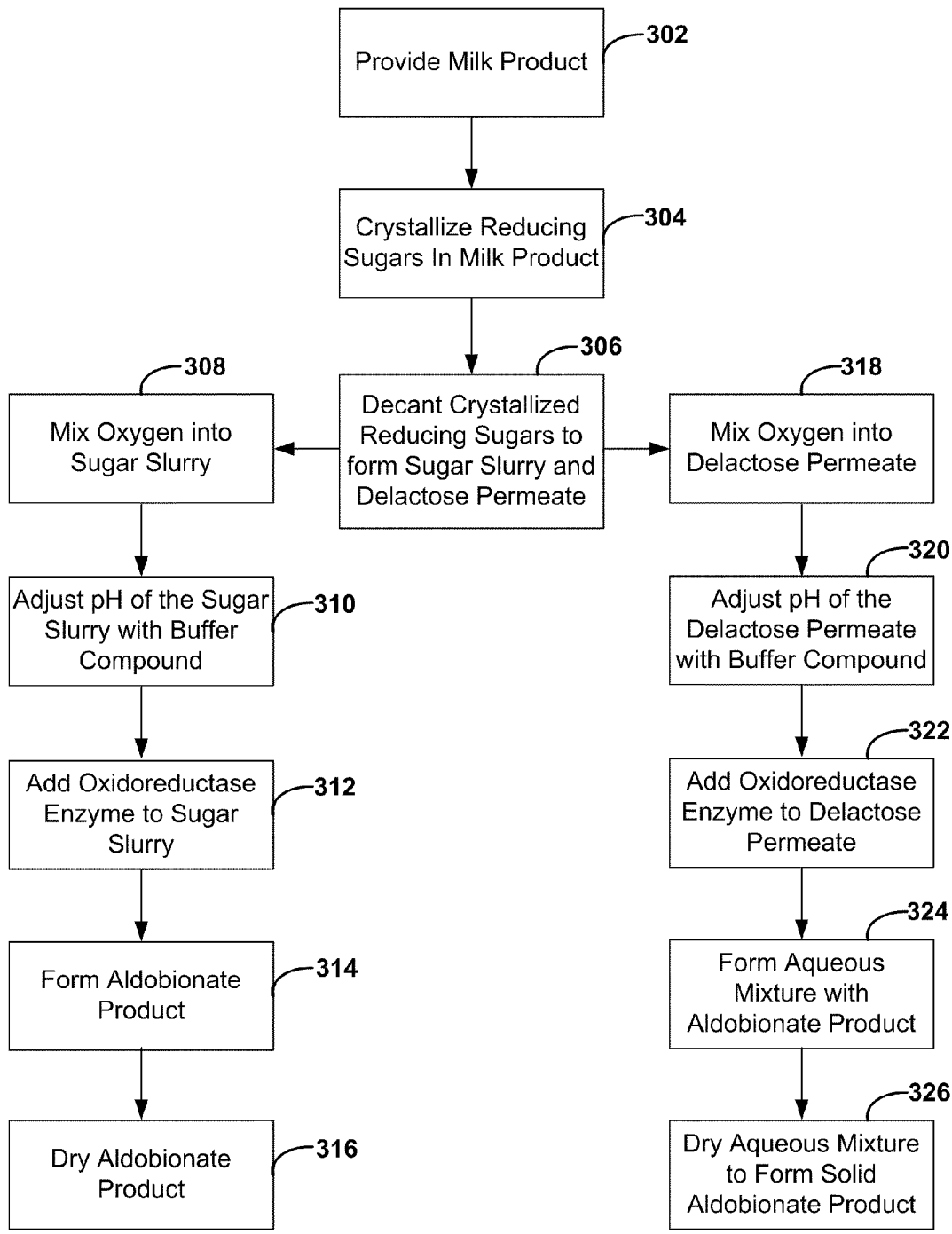
FIG. 3 shows another embodiment of a method 300 of making aldobionate products.

FIG. 3 shows another embodiment of a method 300 of making aldobionate products. The method 300 also starts with providing a milk product 302 and crystallizing a portion of the reducing sugars in the milk product 304 to form a mixture of crystallized reducing sugars and a delactose permeate. Sugar crystallization techniques may include cooling the milk product to a temperature where the dissolved reducing sugars start to crystallize out of solution. The crystallized reducing sugar may be decanted from a delactose permeate (DLP) to form a separated sugar slurry 306. Either or both the sugar slurry and delactose permeate may be treated with oxidoreductase enzymes to make an aldobionate product.

In the case of the sugar slurry, oxygen may be mixed with the slurry 308 and/or the pH of the slurry may be adjusted by addition of a buffer compound 310. Oxidoreductase enzyme is added to the slurry 312 to convert reducing sugars and form a slurry with the aldobionate products 314. The slurry may be dried to form a solid (e.g., powdered) aldobionate product 316.

The delactose permeate also contains residual reducing sugars that may be converted into aldobionate products. This process includes mixing oxygen into the delactose permeate 318 and/or the pH of the permeate may be adjusted by addition of a buffer compound 320. Oxidoreductase enzyme is added to the delactose permeate 322 to convert reducing sugars and form an aqueous mixture with the aldobionate products 324. The mixture may be dried to form a solid (e.g., powdered) aldobionate product 326.

Figure 4:
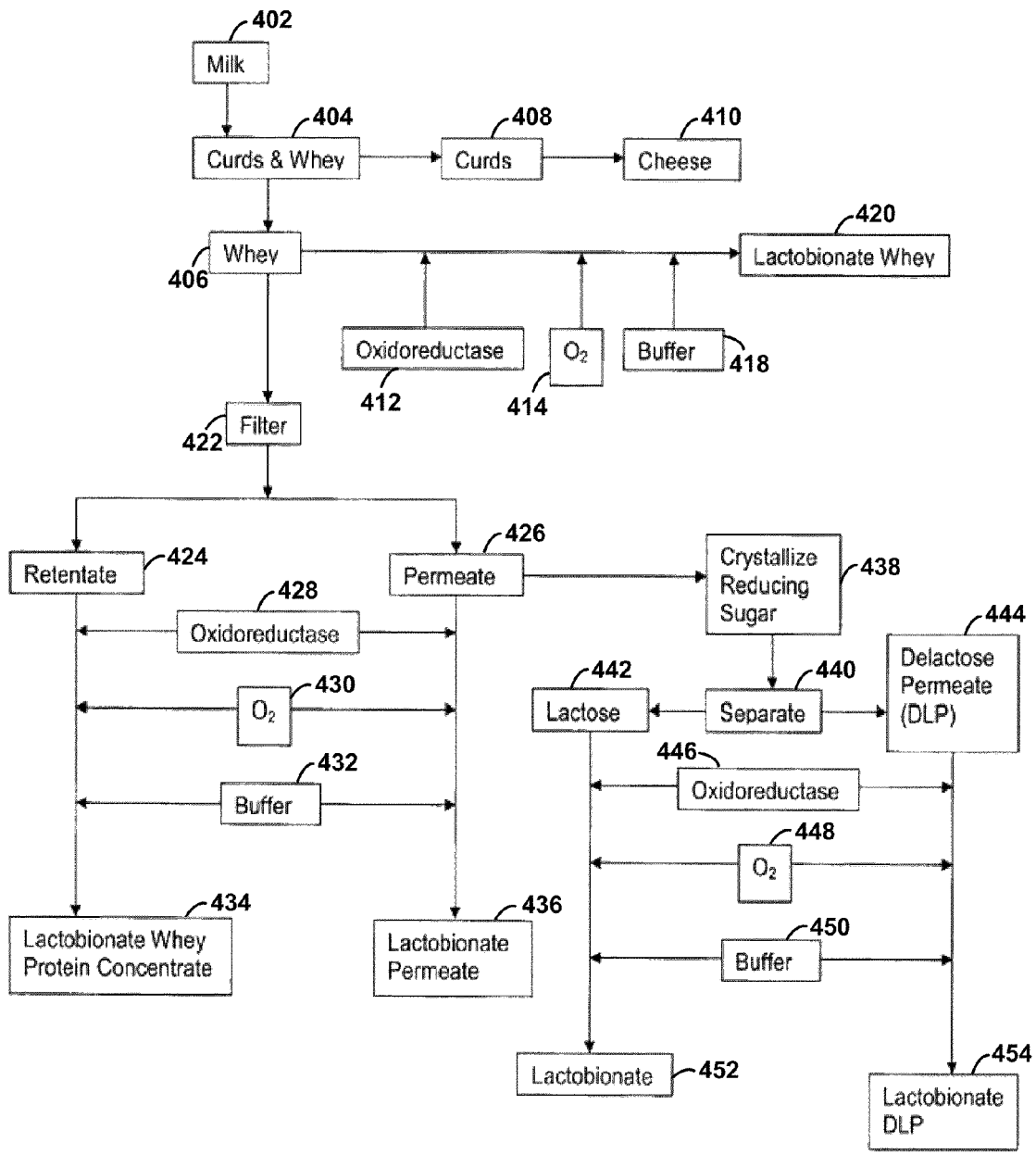
FIG. 4 shows embodiments of a cheesemaking processes 400 are that incorporate methods of converting reducing sugars to aldobionate products at multiple stages.

Referring now to FIG. 4, embodiments of a cheesemaking processes 400 are shown that incorporate methods of converting reducing sugars to aldobionate products at multiple stages. The processes 400 start with taking a milk product 402 and converting it to curds and whey 404 according to a conventional cheesemaking process. The curds 408 may be separated and turned into cheese 410. The raw whey 406 may be converted into an aldobionate product, such as lactobionate whey 420, and/or filtered 432 into a whey permeate 424 and whey retentate 426.

The raw whey 406 is directly converted into lactobionate whey 420, by oxidoreductase enzymes 412 added to the whey 406 that catalytically convert at least a portion of the reducing sugars present into the lactobionic acid and lactobionate salts. The process may also include mixing oxygen 414 into the whey 406 and/or adding a buffer compound 418 to control the pH of the whey 406 during catalysis.

The whey permeate 426 and retentate 424 may also be converted into aldobionate products. The retentate 424 may be mixed with oxygen 430 and buffer compound 432 as oxidoreductase enzymes 428 convert the reducing sugars in the retentate 424 to aldobionate products, and turning the retentate 424 into a lactobionate whey protein concentrate 434. Similarly, the permeate 426 may be mixed with oxygen 430, buffer 432 and oxidoreductase enzymes 428 to form a lactobionate permeate 436 that includes aldobionate products.

The whey permeate 426 may also be treated to crystallize a portion of the reducing sugar 438, and separate 440 the resulting mixture into crystallized lactose 442, and a delactose permeate (DLP) 444. Both the lactose 442 and the DLP 444 may be converted into aldobionic products. The lactose 442 may be mixed with oxidoreductase enzyme 446, oxygen 448, and a pH buffer compound 450. The process converts the lactose solids into lactobionate products 452 and the delactose permeate into a lactobionate DLP 454.

Figure 5:
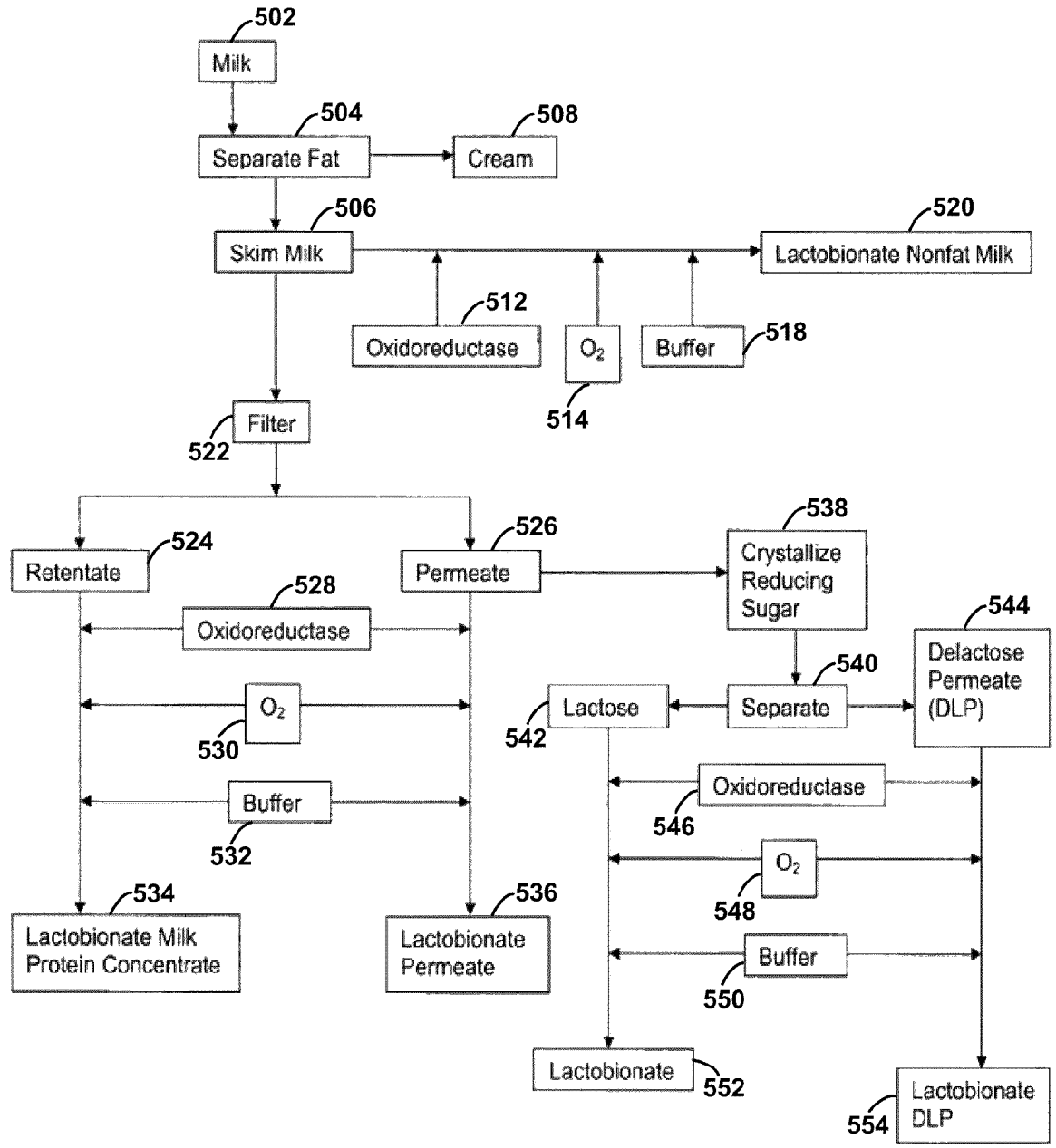
FIG. 5 shows embodiments of processes for making dairy products 500 that incorporate methods of converting reducing sugars to aldobionate products at multiple stages.

FIG. 5 shows embodiments of processes for making dairy products 500 that incorporate methods of converting reducing sugars to aldobionate products at multiple stages. The processes 500 start with taking raw milk 502 and separating the fat 504 to make skim milk 506. The separated fat may be used to make dairy products such as cream 508, while the skim milk may be converted into lactobionate nonfat milk 520 and/or filtered 522 into a skim milk retentate 524 and permeate 526.

The skim milk 506 is directly converted into lactobionate nonfat milk 520, by oxidoreductase enzymes 512 added to the milk 506 that catalytically convert at least a portion of the reducing sugars present into lactobionic acid and/or lactobionate salts. The process may also include mixing oxygen 514 into the milk 506 and/or adding a buffer compound 518 to control the pH of the milk 506 during catalysis.

The skim milk permeate 526 and retentate 524 may also be converted into aldobionate products. The retentate 524 may be mixed with oxygen 530 and buffer compound 532 as oxidoreductase enzymes 528 convert the reducing sugars in the retentate 524 to aldobionate products, and turning the retentate 524 into a lactobionate milk protein concentrate 534. Similarly, the permeate 526 may be mixed with oxygen 530, buffer 532 and oxidoreductase enzymes 528 to form a lactobionate permeate 536 that includes aldobionate products.

The skim milk permeate 526 may also be treated to crystallize a portion of the reducing sugar 538, and separate 540 the resulting mixture into crystallized lactose 542, and a delactose permeate (DLP) 544. Both the lactose 542 and the DLP 544 may be converted into aldobionic products. The lactose 542 may be mixed with oxidoreductase enzyme 546, oxygen 548, and a pH buffer compound 550. The process converts the lactose solids into lactobionate products 552 and the delactose permeate into a lactobionate DLP 554.

It will be appreciated that numerous variations are possible for the processes 400 and 500 described in FIGS. 4 and 5. For example, the raw whey 406 and skim milk 506 may undergo a reducing sugar crystallization process without first being separated into a retentate and permeate. In addition, an actual process may leave out one or more of the routes for making the aldobionate products.

VIII. Methods of Packaging Cheeses and Other Food Products

Conventional methods of packaging cheeses and other food products often require the food products to be packaged in an oxygen-free environment. Typically, the food products are stored in airtight packaging (e.g., sealed plastic) that has been purged of oxygen prior to being sealed. The purging process adds extra expense and complexity to the packaging of food stuffs, but that expense is normally offset by the longer shelf-life of the packaged food.

Methods are contemplated for storing food products (e.g., cheese) in an environment that can include oxygen. Packaging methods may include providing an oxidoreductase enzyme to the food product as a preservative that enhances the storage life of the food. The oxidoreductase enzymes utilize the oxygen in contact with the food to catalyze the oxidation of reducing sugars to aldobionic acids and hydrogen peroxide. The hydrogen peroxide, in turn, helps to preserve the food product. The preservative effect of the oxidoreductase enzymes is enhanced with increased concentrations of oxygen, as the presence of additional oxygen permits the production of more hydrogen peroxide.

Cheeses may be sprayed or otherwise coated with oxidoreductase enzymes. The cheese may be coated prior to or after being placed in a storage container (e.g., a plastic bag). For shredded cheeses, the oxidoreductase enzyme may be added with an anti-caking agent to prevent the cheese from clumping in the packaging. Additional additives and preservatives may also be mixed with the oxidoreductase enzymes and provided to the cheese.

EXAMPLES

Example 1

Calcium lactobionate was generated by combining delactose permeate (DLP), containing approximately 19% lactose, with water to create a 5% lactose solution. Lactose oxidase (Novozymes A/S, Denmark) was added at a rate of 425 units enzyme/kg lactose while catalase (Catazyme 25 L, Novozymes A/S, Denmark) was added at a rate of 6 g/kg lactose. The solution was held at 111° F. (43.9° C.) with a dissolved oxygen content of at least 3.2 mg oxygen/L at a pH between 6.4-6.6 using 5 molar calcium hydroxide. The reaction resulted in a complete conversion of lactose to calcium lactobionate as determined by Capillary Electrophoresis. This solution of calcium lactobionate was then spray dried and added to cheese.

Cheese was manufactured conventionally using starter cultures, modified food starch, and 2% calcium lactobionate (53% moisture, 47 FDB, 5.35 pH, 1.80% salt). The cheese was then shredded and frozen (QLC™).

Two-pound samples bags of frozen cheese were stored in the cooler at 40° F. (4.4° C.) until melted on a deep-dish crust using 10.80-oz of cheese with 3-oz of pizza sauce. The pizza was cooked in Middleby Marshall oven at 420° F. (215.6° C.) for 11 min 30 sec.

The melted pizzas (with 2% calcium lactobionate mixed with cheese and control cheese with non-fat dry milk powder mixed with cheese) were evaluated for blister color, blister % and blister size. The results are shown in Table 1.

It is evident from Table 1 that addition of calcium lactobionate as compared to a combination of modified food starch and dry milk powders had a significant effect in reducing blistering (blister color, % and size), even when up to 2% of a combination of modified food starch and dry milk powders were replaced.

TABLE 1

| Blistering | Control (with nonfat dry milk) Day 2: | Trial (Calcium lactobionate) |
|---|---|---|
| Blister Color* | 14 | 7 |
| Blister %* | 15 | 8 |
| Blister Size* | 6 | 3 |

*Blistering attributes graded on a scale of 1-20 (1 being too low, 20 being too much, and 10 being ideal as described in the following table)

TABLE 1a

|  | NONE (1-4) | SLIGHT (5-8) | MODERATE (8-12) | DEFINITE (13-16) | PRONOUNCED (17-20) |
|---|---|---|---|---|---|
| Blister % | 0-10% | 10-25% | 25-50% | 50-75% | >75% |
| Blister Size | ⅛ to ¼' | ⅜ to ½' | ⅝ to ¾' | ⅞ to 1' | >1' |
| Blister Color | Light Golden | Golden to Light Golden | Brown | Dark Brown | Black |

Example 2

Calcium lactobionate powder, produced by enzymatic conversion of lactose from Leprino Foods, was incorporated into cheese. The cheese was manufactured conventionally using starter cultures, modified food starch, and 2% calcium lactobionate (53% moisture, 47 FDB, 5.35 pH, 1.80% salt). The cheese was then shredded and frozen (QLC™).

Two-pound samples bags of frozen cheese were stored in the cooler at 40° F. (4.4° C.) until melted on a deep-dish crust including 10.80-oz of cheese with 3-oz of pizza sauce. The pizza was cooked in Middleby Marshall oven at 420° F. for 11 min 30 sec.

The melted pizzas (with 2% calcium lactobionate mixed with cheese and control cheese with non-fat dry milk powder mixed with cheese) were evaluated for blister color, blister % and blister size. The results are shown in Table 2.

It is evident from Table 2 that addition of calcium lactobionate as compared to a combination of modified food starch and dry milk powders had a significant effect in reducing blistering (blister color, % and size), even when up to 2% of a combination of modified food starch and dry milk powders were replaced.

TABLE 2

| Blistering | Control (with nonfat dry milk) Day 2: | Trial (Calcium lactobionate) |
|---|---|---|
| Blister Color* | 14 | 10 |
| Blister %* | 15 | 9 |
| Blister Size* | 6 | 3 |

*Blistering attributes graded on a scale of 1-20 (1 being too low, 20 being too much, and 10 being ideal as described in the following table)

TABLE 2a

|  | NONE (1-4) | SLIGHT (5-8) | MODERATE (8-12) | DEFINITE (13-16) | PRONOUNCED (17-20) |
|---|---|---|---|---|---|
| Blister % | 0-10% | 10-25% | 25-50% | 50-75% | >75% |
| Blister Size | ⅛ to ¼' | ⅜ to ½' | ⅝ to ¾' | ⅞ to 1' | >1' |
| Blister Color | Light Golden | Golden to Light Golden | Brown | Dark Brown | Black |

It will be recognized by those of skill in the art that various modifications, alternative constructions, and equivalents may be made to what has been described. Additionally, a number of well known processes and elements have not been described in order to avoid unnecessarily obscuring the description.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is also contemplated. The upper and lower limits of these smaller ranges may independently be included or excluded in the range, and each range where either, neither or both limits are included in the smaller ranges is also contemplated, subject to any specifically excluded limit in the stated range. Where the stated range includes one or both of the limits, ranges excluding either or both of those included limits are also included.

As used herein and in the appended claims, the singular forms "a", "and", and "the" include plural referents unless the context clearly dictates otherwise. Thus, for example, reference to "a process" includes a plurality of such processes and reference to "the electrode" includes reference to one or more electrodes and equivalents thereof known to those skilled in the art, and so forth.

Also, the words "comprise," "comprising," "include," "including," and "includes" when used in this specification and in the following claims are intended to specify the presence of stated features, integers, components, or steps, but they do not preclude the presence or addition of one or more other features, integers, components, steps, or groups.

What is claimed is:

1. A process of making a cheese, the process comprising:
    mixing purified oxygen and an oxidoreductase enzyme with a milk product to form a mixture comprising an aldobionate product;
    combining the mixture with a cheese precursor to make an admixture; and
    heating, kneading and stretching the admixture to form a pasta filata cheese.

2. The process of claim 1, wherein the milk product is selected from the group consisting of whole milk, skim milk, cheese, whey, whey retentate, milk retentate, permeate, lactose, and delactose permeate.

3. The process of claim 1, wherein the pasta filata cheese comprises mozzarella cheese, pizza cheese, provolone cheese, string cheese, or reduced fat cheese.

4. The process of claim 1, wherein the cheese precursor comprises cheese curd.

5. The process of claim 1, wherein the oxidoreductase enzyme catalyzes a reaction between oxygen and a reducing sugar in the milk product to form the aldobionate product.

6. The process of claim 5, wherein the reducing sugar comprises D-glucose, D-galactose, maltose, cellobiose, lactose, D-mannose, D-fructose, and D-xylose.

7. The process of claim 5, wherein the oxidoreductase enzyme is selected from the group consisting of hexose oxidase, glucose oxidase, galactose oxidase, pyranose oxidase, and lactose oxidase.

8. The process of claim 1, wherein the method further comprises mixing a catalase enzyme into the milk product.

9. The process of claim 8, wherein additional oxygen is formed in the milk product by a conversion of hydrogen peroxide to oxygen and water with the catalase enzyme.

10. The process of claim 1, wherein the process further comprises maintaining a pH of the mixture by adding a buffer compound to the milk product.

11. A process of making a pasta filata cheese with a decreased concentration of reducing sugars, the method comprising:
    converting milk into cheese curds;
    heating, kneading and stretching the cheese curds into a cheese mass;
    adding an oxidoreductase enzyme to the cheese mass, wherein at least a portion of the reducing sugars in the cheese mass are converted into aldobionate products by the oxidoreductase enzyme; and
    forming the cheese mass into the pasta filata cheese with the decreased concentration of reducing sugars.

12. The process of claim 11, wherein the aldobionate products comprise aldobionate salts or aldobionate acids.

13. The process of claim 11, wherein the reducing sugars are selected from the group consisting of D-glucose, D-galactose, maltose, cellobiose, lactose, D-mannose, D-fructose, and D-xylose.

14. The process of claim 11, wherein the reducing sugars comprise lactolactone.

15. The process of claim 11, wherein the oxidoreductase enzyme is selected from the group consisting of hexose oxidase, glucose oxidase, galactose oxidase, pyranose oxidase, and lactose oxidase.

16. The process of claim 11, wherein the process further comprises maintaining a pH of the cheese mass by adding a buffer compound to the cheese mass.

17. The process of claim 11, wherein the process further comprises adding a catalase enzyme to the cheese mass, wherein the catalase enzyme converts hydrogen peroxide into molecular oxygen and water.

18. The process of claim 11, wherein the process further comprises adding additional reducing sugars to the cheese mass by adding one or more additional ingredients selected from the group consisting of whole milk, skim milk, whey, whey retentate, milk retentate, permeate, lactose, and delactose permeate, and wherein the additional ingredients are in the form of powder, liquid, or slurry.

19. The process of claim 17, wherein the catalase enzyme and the oxidoreductase enzyme create a reducing sugar oxidation cycle where the oxidoreductase enzyme oxidizes the reducing sugars to the aldobionate products and the hydrogen peroxide, which is converted to the molecular oxygen and water by the catalase enzyme, and wherein the molecular oxygen is used in additional oxidoreductase conversions of reducing sugars.

20. A process of making a pasta filata cheese, the process comprising:
    forming a slurry comprising an oxidoreductase enzyme;
    mixing the slurry with a cheese precursor to form an admixture; and
    heating, kneading and stretching the admixture to form the pasta filata cheese.

21. The process of claim 20, wherein the slurry comprises whole milk, skim milk, cheese, whey, whey retentate, milk retentate, permeate, lactose, or delactose permeate.

22. The process of claim 20, wherein the cheese precursor comprises cheese curd.

23. The process of claim 20, wherein the oxidoreductase enzyme catalyzes a reaction between oxygen and a reducing sugar in the milk product to form the aldobionate product.

24. The process of claim 23, wherein the reducing sugar comprises D-glucose, D-galactose, maltose, cellobiose, lactose, D-mannose, D-fructose, or D-xylose.

25. The process of claim 20, wherein the method further comprises mixing a catalase enzyme into the slurry.

26. The process of claim 20, wherein purified oxygen is mixed into the slurry.

27. The process of claim 25, wherein additional oxygen is formed in the milk product by a conversion of hydrogen peroxide to oxygen and water with the catalase enzyme.

28. The process of claim 20, wherein the process further comprises maintaining a pH of the slurry by adding a buffer compound to the slurry.

* * * * *